United States Patent [19]

Siadak et al.

[11] Patent Number: 5,628,996
[45] Date of Patent: May 13, 1997

[54] **METHOD FOR INHIBITING THE VIABILITY OF *PSEUDOMONAS AERUGINOSA* WITH CROSS-REACTIVE AND CROSS-PROTECTIVE MONOCLONAL ANTIBODIES**

[75] Inventors: Anthony W. Siadak; Mae J. Rosok, both of Seattle, Wash.

[73] Assignee: Bristol-Myers Squibb Company, New York, N.Y.

[21] Appl. No.: 463,910

[22] Filed: Jun. 5, 1995

Related U.S. Application Data

[62] Division of Ser. No. 366,204, Dec. 29, 1994, which is a continuation of Ser. No. 66,604, May 24, 1993, Pat. No. 5,378,812, which is a continuation of Ser. No. 931,179, Nov. 24, 1986, abandoned, which is a continuation-in-part of Ser. No. 807,394, Dec. 10, 1985, abandoned.

[51] Int. Cl.$^6$ .................... A61K 39/395; G01N 33/53; C07K 16/18; C07K 16/12
[52] U.S. Cl. ................................ 424/150.1; 424/142.1; 424/243.1; 424/260.1; 424/170.1; 435/7.2; 435/7.21; 435/7.32; 436/548; 530/387.1; 530/388.15; 530/388.4; 530/809
[58] Field of Search ..................... 424/150.1, 142.1, 424/243.1, 260.1, 170.1; 435/7.2, 7.21, 7.32, 240.27; 436/548; 530/387.1, 388.15, 388.4, 809

[56] References Cited

U.S. PATENT DOCUMENTS

| | | |
|---|---|---|
| 4,464,465 | 8/1984 | Lostrom . |
| 4,587,121 | 5/1986 | Collins et al. . |
| 4,677,070 | 6/1987 | Larrick et al. . |
| 4,734,279 | 3/1988 | Stephan et al. . |
| 4,777,136 | 10/1988 | Young . |
| 4,834,975 | 5/1989 | Siadak et al. . |
| 4,970,070 | 11/1990 | Raff . |

FOREIGN PATENT DOCUMENTS

| | | |
|---|---|---|
| 0101039 | 2/1984 | European Pat. Off. . |
| 0163493 | 4/1985 | European Pat. Off. . |
| 0211353 | 2/1987 | European Pat. Off. . |
| 0256713 | 2/1988 | European Pat. Off. . |
| 84/04458 | 11/1984 | WIPO . |
| 85/01659 | 4/1985 | WIPO . |
| 86/03754 | 7/1986 | WIPO . |

OTHER PUBLICATIONS

Zinner, et al., "Effects of IgM and IgG Antibody in Patients with Bacteremia Due to Gram–Negative Bacilli," *J. Infect. Dis.* 133:37–45 (1976).

Pollack, "Antibody–Mediated Immunity in Pseudomonas Disease and Its Clinical Application," *Immunoglobulins: Characteristics and Uses of Intravenous Preparations,* Alving and Finlayson, eds. pp. 73–79, U.S. Department of Health and Human Services, (1979).

Pollack, et al., "Protective Activity of Antibodies to Exotoxin A and Lipopolysaccharide at the Onset of *Pseudomonas aeruginosa* Septicemia in Man," *J. Clin. Invest.* 63:276–279 (1979).

Clumeck et al., "Humoral Immunity and Circulating Immune Complexes in Gram–Negative Bacteremia and Septic Shock," *bacterial Endotoxins & Host Response,* Agarwal (ed.) Elsevier/North–Holland Biomedical Press, pp. 79–93, (1980).

Koskimies, "Human Lymphoblastoid Cell Line Producing Specific Antibody against Rh–Antigen D," *Scand. J. Immunol.* 11:73–77 (1980).

Hancock, et al., "Monoclonal Antibodies Against *Pseudomonas aeruginosa* Outer Membrane Antigens: Isolation and Characterization," *Infect. Immun.* 37:166–171 (1982).

Sadoff, et al., *Program & abstracts of the Twenty–Second Interscience Conference on Antimicrobiol Agents & Chemotherapy,* Abstract No. 253, (1982).

Pier et al., "Safety and Immunogenicity of High Molecular Weight Polysaccharide Vaccine from Immunotype 1 *Pseudomonas aeruginosa,*" *J. Clin. Invest.* 69:303–308 (1982).

Mackie et al., "Immune Response of the Mouse to Gram–Negative Bacterial Outer Membrane Extracts as Assessed with Monoclonal Antibodies," *J. Immunol.* 129:829–832 (1982).

Liu, et al., "Survey of Heat–Stable, Major Somatic Antigens of *Pseudomonas aeruginosa,*" *Int. J. Systematic Bacteriology* 33:256–264 (1983).

Yarchoan et al., "Limiting Dilution Analysis of Esptein–Barr Virus–Induced Immunoglobulin Production by Human B Cells," *J. Exper. Med.* 157:1–14 (1983).

Cryz et al., "Protection Against *Pseudomonas aeruginosa* Infection in a Murine Burn Wound Sepsis Model by Passive Transfer of Antitoxin A, Antielastase and Antilipopolysaccharide," *Infect. Immun.* 39:1072–1079 (1983).

Lam et al., "Immunogenicity of *Pseudomonas aeruginosa* Outer Membrane Antigens Examined by Crossed Immunoelectrophoresis," *Infect Immun.* 42:88–98 (1983).

Darveau, et al., "Procedure for Isolation of Bacterial Lipopolysaccharides from Both Smooth and Rough *Pseudomonas aeruginosa* and *Salmonella typhimurium* strains," *J. Bacteriol.* 155:831–838 (1983).

Collins, et al., "Protective Activity of an Intravenous Immune Globulin (Human) Enriched in Antibody against Lipopolysaccharide Antigens of *Pseudomonas aeruginosa,*" *Am. J. Med.* pp. 168–174 (1984).

(List continued on next page.)

*Primary Examiner*—James C. Housel
*Assistant Examiner*—Susan A. Loring
*Attorney, Agent, or Firm*—Townsend and Townsend and Crew LLP

[57] ABSTRACT

Cell lines have been produced that secrete human monclonal antibodies capable of binding to the lipopolysaccharide molecules of selected *Pseudomonas aeruginosa* IATS serotypes. Pharmaceutical compositions containing these antibodies, which can be in combination with other monoclonal antibodies, blood plasma fractions and antimicrobial agents, and the prophylactic and therapeutic use of such compositions in the management of infections are included.

10 Claims, No Drawings

OTHER PUBLICATIONS

Pier et al., "Immunochemical Characterization of High-Molecular-Weight Polysaccharide From Fisher Immunotype 3 *Pseudomonas aeruginosa*," *Infect. Immun.* 45:309–313 (1984).

Sawada et al., "Protection Against Infection with *Pseudomonas aeruginosa* by Passive Transfer of Monoclonal Antibodies to Lipopolysaccharides and Outer Membrane Proteins," *J. Infect. Dis.* 150:570–576 (1984).

Steinitz et al., "Human Anti–Pneumococci Antibody Produced by an Epstein Barr Virus (EBV)–Immortalized Cell Line," *J. Immunol.* 132:877–882 (1984).

Teng et al., "Protection against Gram–Negative Bacteremia and Endotoxemia with Monoclonal IgM Antibodies," *Proc. Natl. Acad. Sci. USA* 82:1790–1794 (1985).

Sadoff et al., "Characterization of Mouse Monoclonal Antibodies Directed against *Pseudomonas aeruginsoa* Lipopolysaccharides," *Antibiot. Chemother.* 36:134–146 (1985).

Sawada et al., "Characterization of a Human Monoclonal Antibody to Lipopolysaccharides of *Pseudomonas aeruginosa* Serotype 5: A Possible Candidate as an Immunotherapeutic Agent for Infections with *P. aeruginosa*," *J. Infect. Dis.* 152:965–970 (1985).

Siadak and Lostrom, "Cell–Driven Viral Transformation," *Human Hybridomas & Monoclonal Antibodies*, Engleman et al., eds. Plenum Publishing Corp., pp. 167–185 (1985).

Hornberger et al., "Human Monoclonal Antibodies Against Gram–Negative Bacteria," *Fed. Am. Soc. Exp. Biol.*, 69th Annual Meeting, Abstracts of Papers, No. 5366 (1985).

Larrick et al., "Generation and Characterization of Human Monoclonal Anti–*Pseudomonas aeruginosa* Antibodies," *Human Hybridomas: Diagnostic and Therapeutic Applications* in A.J. Strelkaukas (ed.) pp. 65–80 (1987).

Larrick, U.S. Statutory Invention Reg. No. H494, Jul. 5, 1988.

Zweerink et al., "Human Monoclonal Antibodies that Protect Mice against Challenge with *Pseudomonas aeruginosa*," *Infect. Immun.* 56:1873–1879 (1988).

Lang et al., "Isolation and Characterization of a Human Monoclonal Antibody that Recognizes Epitopes Shared by *Pseudomonas aeruginosa* Immunotype 1, 3, 4 and 6 Lipopolysaccharides," *Infect. Immun.* 57:1873–1879 (1989).

Hector et al., "Treatment of Experimental *Pseudomonas aeruginosa* Pneumonia with a Human IgM Monoclonal Antibody," *J. Infect. Dis.* 160:483–489 (1989).

Lang et al., "Immunoprotective Capacities of Human and Murine Monoclonal Antibodies Recognizing Serotype–Specific and Common Determinants of Gram–negative Bacteria," *Therapeutic Monoclonal Antibodies*, Borrebaeck and Larrick, eds., pp. 223–234 (1990).

Verhoef, et al., "Prospects for Monoclonal Antibodies in the Diagnosis and Treatment of Bacterial Infections," *J. Clin. Microbiol. Infect. Dis.* 9:247–250 (Apr., 1990).

Cross, et al., "Choice of Bacteria in Animal Models of Sepsis," *Infect. Immun.*, 61(7):2741–2747 (Jul., 1993).

METHOD FOR INHIBITING THE VIABILITY OF *PSEUDOMONAS AERUGINOSA* WITH CROSS-REACTIVE AND CROSS-PROTECTIVE MONOCLONAL ANTIBODIES

CROSS-REFERENCE TO RELATED APPLICATIONS

This application is a divisional of Ser. No. 08/366,204, filed Dec. 29, 1994 (pending), which is a continuation of Ser. No. 08/066,604, filed May 24, 1993 (now U.S. Pat. No. 5,378,812), which is a continuation of Ser. No. 06/931,179, filed Nov. 24, 1986 (now abandoned), which is a continuation-in-part of Ser. No. 06/807,394, filed Dec. 10, 1985 (now abandoned), which are incorporated herein by reference.

FIELD OF THE INVENTION

The present invention relates to the application of immunological techniques to provide novel materials useful in diagnosing and treating bacterial infections and, more particularly, to the production and application of human monoclonal antibodies that are capable of recognizing multiple serotypes of *Pseudomonas aeruginosa*.

BACKGROUND OF THE INVENTION

Gram-negative disease and its most serious complications, e.g., bacteremia and endotoxemia, are the cause of significant morbidity and mortality in human patients. This is particularly true of the gram-negative organism *Pseudomonas aeruginosa*, which has been increasingly associated with bacterial infections, especially nosocomial infections, over the last fifty years.

During the past few decades, antibiotics have been the therapy of choice for control of gram-negative disease. The continued high morbidity and high mortality associated with gram-negative bacterial disease, however, is indicative of the limitations of antibiotic therapy particularly with respect to *P. aeruginosa*. (See, for example, Andriole, V. G., "Pseudomonas Bacteremia: Can Antibiotic Therapy Improve Survival?", *J. Lab. Clin. Med.* (1978) 94:196–199). This has prompted the search for alternative methods of prevention and treatment.

One method that has been considered is augmentation of the host's immune system by active or passive immunization. For instance, it has been observed that active immunization of humans or experimental animals with whole cell bacterial vaccines or purified bacterial endotoxins from *P. aeruginosa* leads to the development of specific opsonic antibodies directed primarily against determinants on the repeating oligosaccharide units of the lipopolysaccharide (LPS) molecules located on the outer cell membrane of *P. aeruginosa* (see Pollack, M., *Immunoglobulins: Characteristics and Uses of Intravenous Preparations*, Alving, B. M. and Finlayson, J. S., eds, pp. 73–79, U.S. Department of Health and Human Services, 1979). Such antibodies, whether actively engendered or passively transferred, have been shown to be protective against the lethal effects of *P. aeruginosa* infection in a variety of animal models (Pollack, Supra) and in some preliminary investigations with humans (see Young, L. S. and Pollack, M., *Pseudomonas aeruginosa*, Sabath, L., ed., pp. 119–132, Hans Huber, 1980). Moreover, of particular importance to the role of these antibodies in humans has been the finding in patients with *P. aeruginosa* bacteremia of an association between survival and high acute serum titers of antibodies to the LPS molecules of the infecting strain (see Pollack, M., and Young, L. S., *J. Clin Invest.*, 63:276–286, (1979)).

The above reports suggest that immunotherapeutic approaches could be utilized to prevent and treat bacterial disease due to *P. aeruginosa*, such as by administering pooled human immune globulins that contain antibodies against the infecting strain(s). Human immune globulins are defined herein as that portion of fractionated human plasma that is enriched for antibodies, among which are represented specific antibodies to strains of *P. aeruginosa*. Due to certain inherent limitations in using human immune globulin components, this approach to treatment of disease due to *P. aeruginosa* remains under investigation (see, for example, Collins, M. S. and Roby, R. E., Am. J. Med., 76(3A):168–174, (1984)), and as yet there are no commercial products available utilizing these components.

One such limitation associated with immune globulin compositions is that they consist of pools of samples from a thousand or more donors, such samples having been preselected for the presence of particular anti-Pseudomonas antibodies. This pooling leads to an averaging of individual antibody titers which, at best, results in modest increases in the resultant titer of the desired antibodies.

Another limitation is that the preselection process itself requires expensive, continuous screening of the donor pool to assure product consistency. Despite these efforts, the immune globulin products can still have considerable variability from batch to batch and among products from different geographic regions.

Yet another such limitation inherent in immune globulin compositions is that their use results in the coincident administration of large quantities of extraneous proteinaceous substances (which may include viruses, such as those recently shown to be associated with Acquired Immune Deficiency Syndrome, or AIDS), having the potential to cause adverse biologic effects. The combination of low titers of desired antibodies and high content of extraneous substances may often limit, to suboptimal levels, the amount of specific and thus beneficial immune globulin(s) administrable to the patient.

There exists in the literature a number of serotyping schema that are useful for analyzing *Pseudomonas, aeruginosa* infections. The schema are primarily based on the heat-stable major somatic antigens of this organism (see Zierdt, C. H., in *Glucose Nonfermenting Gram-Negative Bacteria In Clinical Microbiology*, Gilardi, G. L., ed., CRC Press, pp. 213–238 (1978)). The proliferation of the serogrouping schema has made serological studies of *P. aeruginosa* rather difficult to compare, and thus the choice of any given system for the purpose of screening supernatants would seem somewhat arbitrary. The confusion between typing systems was recently clarified by the creation of the International Antigenic Typing Scheme (IATS) system which was proposed by the Subcommittee on Pseudomonadaceae of the International Committee on Systematic Bacteriology as the backbone for further serological study of *P. aeruginosa*. This system, which provides for seventeen distinct serotypes, designated IATS Type 1, IATS Type 2, etc., encompasses all the heat-stable major somatic antigens identified in previous systems. See Liu, P. V., Int. J. Syst. Bacteriol., 33:256–264, (1983), which is incorporated herein by reference.

In developing protective monoclonal antibodies that are cross-reactive among strains of *P. aeruginosa*, it is also advantageous to incorporate a typing scheme which is based on the protective antigens of *P. aeruginosa*. Such a scheme has been devised with the intention of developing a vaccine for clinical use and is described in detail in Fisher, M. W. et al., J. Bacteriol., 98:835–836, (1969). This system, commonly referred to as the Fisher typing system, classifies the majority of known P. aeruginosa into seven types, designated Fisher immunotype 1, Fisher immunotype 2, etc. Correlation between the IATS and Fisher typing systems has been clarified (see Liu, P. V., et al., supra) and is presented in Table I. As noted in Table I, there are no corresponding Fisher immunotypes for certain IATS serotypes, although each Fisher immunotype does correspond to a certain IATS serotype. For the IATS and Fisher typing systems, the antigenic determinants relevant to both serotyping schemes are believed to reside on the surface LPS molecules of P. aeruginosa (Liu, P. V. et al., supra; Hanessien, F., et al., Nature, 229:209–210 (1979)).

TABLE I

Comparison and Correlation of the IATS and Fisher Typing Schemes for Pseudomonas aeruginosa

| IATS | Fisher |
| --- | --- |
| 1 | 4 |
| 2 | 3 |
| 3 | — |
| 4 | — |
| 5 | 7 |
| 6 | 1 |
| 7 | — |
| 8 | 6 |
| 9 | — |
| 10 | 5 |
| 11 | 2 |
| 12 | — |
| 13 | — |
| 14 | — |
| 15 | — |
| 16 | — |
| 17 | — |

In 1975 Kohler and Milstein reported their seminal discovery that certain mouse cell lines could be fused with mouse spleen cells to create hybridomas each of which which would secrete antibodies of a single specificity, i.e., monoclonal antibodies (Kohler, G., and Milstein, C., Nature, 256:495–497 (1975)). With the advent of this technology it became possible, in some cases, to produce large quantities of exquisitely specific murine antibodies to a particular determinant or determinants on antigens. Such mouse monoclonal antibodies or compositions of such antibodies may, however, have major disadvantages for use in humans, particularly in light of the finding that mouse monoclonal antibodies when used in trial studies for the treatment of certain human disease have often been observed to elicit an immune response that renders them noneffective (Levy, R. L. and Miller, R. A., Ann. Rev. Med., 34:107–116, (1983)).

Using hybridoma technology, Sadoff et al. have reported the production of a mouse monoclonal antibody of the IgM class directed against an O-side chain determinant on the LPS molecules of a particular serotype of P. aeruginosa (Abstracts of the 1982 Interscience Conference on Antimicrobial Agents and Chemotherapy, No. 253). They further reported that this murine antibody protected mice against a lethal challenge of P. aeruginosa of the same serotype as the type to which the antibodies were directed (i.e., the homologous serotype). Several subsequent articles have detailed the development of mouse and human anti-P. aeruginosa LPS monoclonal antibodies of various specificities; for example: Sawada, S., et al., J. Inf. Dis., 150:570–576, (1984); Sadoff, J., et al., Antibiot. Chemother., 26:134–146, (1985); Hancock, R., et al., Infect. Immun. 37:166–171 (1982); Siadak, A. W. and Lostrom, M. E., in Human Hybridomas and Monoclonal Antibodies, Engleman, E. G., et al., eds., pp. 167–185, Plenum Publishing Corp. (1985) and Sawada, S. et al., J. Inf. Dis., 152:965–970, (1985). Production and immunotherapeutic application of anti-P. aeruginosa LPS serotype-specific human monoclonal antibodies are disclosed in pending U.S. patent application Ser. Nos. 734,624 and 828,005, which are incorporated herein by reference.

While certain advantages may exist for utilizing monoclonal antibodies specific for a single IATS serotype of P. aeruginosa in some situations, such as when infection can be traced to a single serotype, in many other situations they would not be preferred. For example, in prophylactic treatments for potential infections in humans, it would be preferable to administer a human antibody or antibodies protective against a plurality of IATS serotypes. Similarly, in therapeutic applications where the serotype(s) of the infecting strain(s) is not known, it would be preferable to administer a human antibody or antibodies effective against most, if not all, of the clinically important P. aeruginosa IATS serotypes. Whereas a combination of human monoclonal antibodies, each specific for a single IATS serotype of P. aeruginosa, theoretically might be formulated to protect against the various serotypes, such a composition would be difficult to develop and, from a manufacturing standpoint, uneconomical to produce.

Accordingly there exists a significant need for human anti-P. aeruginosa monoclonal antibodies capable of recognizing and providing protection against multiple IATS serotypes of P. aeruginosa. Further, these antibodies should be suitable for use as prophylactic and therapeutic treatments of P. aeruginosa infections. The present invention fulfills these needs.

SUMMARY OF THE INVENTION

Novel cell lines are provided Which can produce human monoclonal antibodies capable of specifically reacting with the LPS molecules of a plurality of, but not all, IATS serotypes of P. aeruginosa. These antibodies have various reactivities with Fisher immunotypes, binding to zero, one, or a plurality of immunotypes. Additionally, a method is provided for treating a human susceptible to infection or already infected with P. aeruginosa by administering a prophylactic or therapeutic amount of a composition comprising at least one human monoclonal antibody or binding fragment thereof capable of cross-reacting with P. aeruginosa IATS serotypes, the composition preferably also including a physiologically acceptable carrier. The composition may also contain any one or more of the following: additional human monoclonal antibodies capable of reacting with P. aeruginosa flagella, exotoxin A, or with other serotype or immunotype determinants on the LPS of P. aeruginosa; a gamma globulin fraction from human blood plasma; a gamma globulin fraction from human blood plasma, where the plasma is obtained from humans exhibiting elevated levels of immunoglobulins reactive with P. aeruginosa; and one or more antimicrobial agents.

DESCRIPTION OF THE SPECIFIC EMBODIMENTS

In accordance with the present invention, novel cells capable of producing human monoclonal antibodies and compositions comprising such antibodies are provided, such compositions being capable of selectively recognizing at least a plurality of, and in some cases all, *P. aeruginosa* strains, where individual antibodies typically recognize multiple IATS serotypes and zero, one or more Fisher immunotypes of *P. aeruginosa*. The subject cells have identifiable chromosomes in which the germ-line DNA from them or precursor cells have been rearranged to encode an antibody having a binding site for an epitope common among certain *P. aeruginosa* serotypes. These human monoclonal antibodies can be used in a wide variety of ways, including diagnosis and therapy (e.g., protective in vivo).

Typically, the cells of the present invention will be human transformed lymphocytes that produce protective human monoclonal antibodies to accessible LPS molecules of *P. aeruginosa*. By "accessible" is meant that the LPS molecules are physically available in the environment of use for direct interaction with the monoclonal antibodies. The monoclonal antibodies so provided are useful in the treatment or prophylaxis of serious disease due to *P. aeruginosa*. The LPS molecules of the outer membrane of 2. aeruginosa would be available for direct contact by the antibody molecules, thus facilitating complement-mediated lysis and/ or phagocytosis of the organism. Furthermore, those LPS molecules that are shed from the outer membrane into the surrounding environment would also be free to interact directly with the antibody molecules and be cleared via the reticuloendothelial system.

The preparation of monoclonal antibodies can be accomplished by immortalizing the expression of nucleic acid sequences that code for antibodies specific for an epitope on the LPS molecules of multiple serotypes of *P. aeruginosa*. Typically the monoclonal antibodies are produced by cell-driven Epstein-Barr virus (EBV) transformation of human B-lymphocyte cells obtained from human donors who have been exposed to the appropriate serotype(s) of *P. aeruginosa*. The antibody secreting cell lines so produced are characterized as continuously growing lymphoblastoid cells that possess a diploid karyotype, are Epstein-Barr nuclear antigen positive, and secrete monoclonal antibody of either IgG, IgM, IgA, or IgD isotype, including various subtypes such as IgG1, IgG2, IgG3 and IgG4. The cell-driven transformation process itself is described in detail in U.S. Pat. No. 4,464,465, which is incorporated herein by reference. The monoclonal antibodies may be used intact, or as fragments, such as Fv, Fab, F(ab')$_2$, but usually intact, prepared in accordance with procedures well-known in the art.

Alternatively, cell lines producing the antibodies could be produced by cell fusion between suitably drug-marked human myeloma, mouse myeloma, human-mouse heteromyeloma, or human lymphoblastoid cells with human B-lymphocytes to yield human hybrid cell lines.

The cell lines of the present invention may find use other than for the direct production of the human monoclonal antibodies. The cell lines may be fused with other cells (such as suitably drug-marked human myeloma, mouse myeloma, human-mouse heteromyeloma, or human lymphoblastoid cells), to produce hybridomas, and thus provide for the transfer of the genes encoding the monoclonal antibodies. Alternatively, the cell lines may be used as a source of the chromosomes encoding the immunoglobulins, which may be isolated and transferred to cells by techniques other than fusion. In addition, the genes encoding the monoclonal antibodies may be isolated and used in accordance with recombinant DNA techniques for the production of the specific immunoglobulin in a variety of hosts. Particularly, by preparing cDNA libraries from messenger RNA, a single cDNA clone, coding for the immunoglobulin and free of introns, may be isolated and placed into suitable prokaryotic or eukaryotic expression vectors and subsequently transformed into a host for ultimate bulk production.

The lymphoblastoid or hybrid cell lines may be cloned and screened in accordance with conventional techniques, with the antibodies that are capable of binding to the epitopes of different *P. aeruginosa* IATS serotypes and Fisher immunotypes detected in the cell supernatants. By utilizing antibodies of the present invention as blocking antibodies in screening, in accordance with procedures well-known to those skilled in the art, additional monoclonal antibodies recognizing the same antigenic determinants or epitopes can be readily isolated.

In one aspect of the present invention, human monoclonal antibodies are provided that are capable of specifically binding to the lipopolysaccharide determinants present on a plurality of, but not all, IATS serotypes of *P. aeruginosa*. These determinants may be present, for example, on two or three IATS serotypes, and on zero, one, or at least two Fisher immunotypes. Such antibodies may be protective in vivo against some or all of the recognized serotypes and immunotypes, typically two or more serotypes.

Monoclonal antibodies of the present invention can also find a wide variety of utilities in vitro. By way of example, the monoclonal antibodies can be utilized for typing, for isolating specific *P. aeruginosa* strains, for selectively removing *P. aeruginosa* cells in a heterogeneous mixture of cells, or the like.

For diagnostic purposes, the monoclonal antibodies may either be labeled or unlabeled. Typically, diagnostic assays entail detecting the formation of a complex through the binding of the monoclonal antibody to the LPS of the *P. aeruginosa* organism. When unlabeled, the antibodies find use in agglutination assays. In addition, unlabeled antibodies can be used in combination with other labeled antibodies (second antibodies) that are reactive with the monoclonal antibody, such as antibodies specific for immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some include those described in U.S. Pat. Nos. 3,817,827; 3,850,752; 3,901, 654; 3,935,074; 3,984,533; 3,996,345; 4,034,074; and 4,098,876, all of which are incorporated herein by reference.

Commonly, the monoclonal antibodies of the present invention are utilized in enzyme immunoassays, where the subject antibodies, or second antibodies from a different species, are conjugated to an enzyme. When a sample containing *P. aeruginosa* of a certain serotype, such as human blood or lysate thereof, is combined with the subject antibodies, binding occurs between the antibodies and those molecules exhibiting the desired epitope. Such cells may then be separated from the unbound reagents, and a second antibody (labeled with an enzyme) added. Thereafter, the presence of the antibody-enzyme conjugate specifically bound to the cells is determined. Other conventional techniques well known to those skilled in the art may also be utilized.

Kits can also be supplied for use with the subject antibodies in the detection of *P. aeruginosa* infection or for the presence of *P. aeruginosa* antigen. Thus, the subject monoclonal antibody composition of the present invention may be provided, usually in a lyophilized form, either alone or in conjunction with additional antibodies specific for other gram-negative bacteria. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

PHARMACEUTICAL FORMULATIONS AND USE

The monoclonal antibodies of this invention can also be incorporated as components of pharmaceutical compositions containing a therapeutic or prophylactic amount of at least one of the monoclonal antibodies of this invention with a pharmaceutically effective carrier. A pharmaceutical carrier should be any compatible, non-toxic substance suitable to deliver the monoclonal antibodies to the patient. Sterile water, alcohol, fats, waxes, and inert solids may be used as the carrier. Pharmaceutically accepted adjuvants (buffering agents, dispersing agents) may also be incorporated into the pharmaceutical composition. Such compositions can contain a single monoclonal antibody so as to be specific for two or more, but not all IATS serotypes of P. aeruginosa. Alternatively, a pharmaceutical composition can contain two or more monoclonal antibodies to form a "cocktail." For example, a cocktail containing human monoclonal antibodies against groups of the various P. aeruginosa serotypes and immunotypes would be a universal product with activity against the great majority of the clinical isolates of that particular bacterium.

Of interest are prophylactic and/or therapeutic monoclonal antibody compositions capable of reacting with at least three IATS serotypes, usually at least four, and more usually at least five IATS serotypes. Of particular interest are monoclonal antibody compositions which react with at least about seven, preferably at least about ten to fourteen and up to and including all seventeen IATS serotypes. In conjunction with the IATS serotypes, desirably the compositions will react with at least one, usually at least two, and more usually at least three or four and up to and including all seven immunotypes of the Fisher immunotyping system.

Each of the compositions will include at least one, usually at least two, and more usually at least three antibodies or more, where each antibody reacts with at least 2, 3, 4, or more, but not all, IATS serotypes. Desirably there will be at least one monoclonal antibody which binds to at least two IATS serotypes and one or more Fisher immunotypes, preferably at least two immunotypes.

Desirably, the total number of different monoclonal antibodies in a composition will be at least one and equal to or less than about one-half the total number of IATS serotypes with which the compositions reacts, frequently one-third such total number.

The mole ratio of the various monoclonal antibody components will usually not differ by more than a factor of 10, more usually by not more than a factor of 5, and will usually be in a mole ratio of about 1:1–2 to each of the other antibody components.

The human monoclonal antibodies of the present invention may also be used in combination with other monoclonal antibody compositions or with existing blood plasma products, such as commercially available gamma globulin and immune globulin products used in prophylactic or therapeutic treatment of P. aeruginosa disease in humans. Preferably, for immune globulins the plasma will be obtained from human donors exhibiting elevated levels of immunoglobulins reactive with P. aeruginosa. See generally, the compendium "Intravenous Immune Globulin and the Compromised Host," Amer. J. Med., 76(3a), Mar. 30, 1984, pgs 1–231, which is incorporated herein by reference.

The monoclonal antibodies of the present invention can be used as separately administered compositions given in conjunction with antibiotics or antimicrobial agents. Typically, the antimicrobial agents may include an antipseudomonal penicillin (e.g., carbenicillin) in conjunction with an aminoglycoside (e.g., gentamicin, tobramycin, etc.), but numerous additional agents (e.g., cephalosporins) well-known to those skilled in the art may also be utilized.

The human monoclonal antibodies and pharmaceutical compositions thereof of this invention are particularly useful for oral or parenteral administration. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least about 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water, and 50 mg of monoclonal antibody. A typical composition for intravenous infusion could be made up to contain 250 ml of sterile Ringer's solution, and 150 mg of monoclonal antibody. Actual methods for preparing parenterally administrable compositions will be known or apparent to those skilled in the art and are described in more detail in, for example, Remington's Pharmaceutical Science, 15th Ed., Mack Publishing Company, Easton, Pa. (1980), which is incorporated herein by reference.

The monoclonal antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss, than IgG antibodies) and that use levels may have to be adjusted to compensate.

The compositions containing the present human monoclonal antibodies or a cocktail thereof can be administered for the prophylactic and/or therapeutic treatment of *P. aeruginosa* infections. In therapeutic application, compositions are administered to a patient already infected with one or more *P. aeruginosa* serotypes, in an amount sufficient to cure or at least partially arrest the infection and its complications. An amount adequate to accomplish this is defined as a "therapeutically effective dose." Amounts effective for this use will depend upon the severity of the infection and the general state of the patient's own immune system, but generally range from about 1 to about 200 mg of antibody per kilogram of body weight with dosages of from 5 to 25 mg per kilogram being more commonly used. It must be kept in mind that the materials of this invention may generally be employed in serious disease states, that is life-threatening or potentially life-threatening situations especially bacteremia and endotoxemia due to *P. aeruginosa*. In such cases, in view of the absence of extraneous substances and the absence of "foreign substance" rejections which are achieved by the present human monoclonal antibodies of this invention, it is possible and may be felt desirable by the treating physician to administer substantial excesses of these antibodies.

In prophylactic applications, compositions containing the present antibody or a cocktail thereof are administered to a patient not already infected by *P. aeruginosa* to enhance the patient's resistance to such potential infection. Such an amount is defined to be a "prophylactically effective dose." In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

EXPERIMENTAL

Example I

Example I demonstrates methods for the production of human monoclonal antibodies (IgM isotype) that react with IATS serotypes 2, 5, and 16 and Fisher immunotypes 3 and 7.

A peripheral blood sample obtained from a cystic fibrosis patient known to have had chronic infection with *P. aeruginosa* served as a source of human B cells. Mononuclear cells were separated from the blood by standard centrifugation techniques on Ficoll-Paque (Boyum, A., *Scand. J. Clin. Lab. Invest.* (1968) 21:Suppl. 97, 77–89) and washed twice in calcium/magnesium-free phosphate buffered saline (PBS).

The mononuclear cells were depleted of T-cells using a modified E-rosetting procedure. Briefly, the cells were first resuspended to a concentration of $1 \times 10^7$ cells/ml in PBS containing 20% fetal calf serum (FCS) at 4° C. One ml of this suspension was then placed in a 17×100 mm polystyrene round bottom tube to which was added $1 \times 10^9$ 2-aminoisothiouronium bromide (AET)-treated sheep red blood cells from a 10% (v/v) solution in Iscove's modified Dulbecco's medium (Iscove's medium) (Madsen, M. and Johnson, H. E., *J. Immun. Methods* (1979) 27:61–74). The suspension was very gently mixed for 5–10 minutes at 4° C. and the E-rosetted cells then removed by centrifugation on Ficoll-Paque for 8 minutes at 2500×g at 4° C. E-rosette negative peripheral blood mononuclear cells (E⁻PBMC) banding at the interface were collected and washed once in Iscove's medium and resuspended in same containing 15% (v/v) FCS, L-glutamine (2 mmol/l), penicillin (100 IU/ml), streptomycin (100 μg/ml), hypoxanthine ($1 \times 10^{-4}$M), aminopterin ($4 \times 10^{-7}$M), and thymidine ($1.6 \times 10^{-5}$M). This medium is hereafter referred to as HAT medium.

Cell-driven transformation of the E⁻PBMC was accomplished by co-cultivating these cells with a transforming cell line. The transforming cell line was an Epstein-Barr nuclear antigen (EBNA) positive human lymphoblastoid cell line derived by ethyl methanesulphonate (EMS) mutagenesis of the GM 1500 lymphoblastoid cell line followed by selection in the presence of 30 μg/ml 6-thioguanine to render the cells hypoxanthine-guanine phosphoribosyl transferase (HGPRT) deficient and thus HAT sensitive. This cell line is denominated the 1A2 cell line and was deposited at the American Type Culture Collection (A.T.C.C.) on Mar. 29, 1982, under A.T.C.C. No. CRL 8119. 1A2 cells in logarithmic growth phase were suspended in HAT medium and then combined with the E⁻PBMC at a ratio of eight 1A2 cells per E⁻PBMC. The cell mixture was plated into eight round-bottom 96-well microtiter plates (Costar 3799) at a concentration of 72,000 cells/well in a volume of 200 μl per well, and incubated at 37° C. in a humidified atmosphere containing 6% $CO_2$. Cultures were fed on days 5 and 8 post-plating by replacement of half the supernatant with fresh HAT medium. The wells were observed every other day on an inverted microscope for signs of cell proliferation. Twelve days post plating, it was observed that 100% of the wells contained proliferating cells and that in most of the wells, the cells were of sufficient density for removal and testing of supernatants for anti-*P. aeruginosa* antibody.

Supernatants were screened for the presence of anti-*P. aeruginosa* antibodies using an enzyme linked immunosorbent assay (ELISA) technique (Engvall, E., (1977) 55:193–200). Antigen plates consisted of flat-bottom 96-well microtiter plates (Immulon II, Dynatech), the wells of which contained various live bacteria adsorbed to the bottom of the well. To facilitate adsorption of the bacteria to the plastic, 50 μl/well of poly-L-lysine (PLL) (1 μg/ml in PBS, pH 7.2) was incubated for 30 minutes at room temperature. The unadsorbed PLL was then flicked out, the plates washed once with PBS, 50 μl of washed bacterial suspension ($OD_{660}$=0.2) in PBS added to each well, and the plates incubated for one hour at 37° C. Unadsorbed bacteria were removed by washing the plates three times with saline-Tween [0.9% NaCl, 0.05% (v/v) Tween-20]. Various antigen plates used in the screen included: (1) a mixture of *P. aeruginosa* Fisher immunotypes 1, 2, and 4 (A.T.C.C. Nos. 27312, 27313, 27315); (2) a mixture of *P. aeruginosa* Fisher immunotypes 3, 5, 6, and 7 (A.T.C.C. Nos. 27314, 27316, 27317, 27318, respectively); and (3) a microtiter plate with no bacteria.

The ELISA was initiated by first blocking the plates with 200 μl/well of blocking buffer [PBS, pH 7.2, containing 5% (w/v) non-fat dry milk, 0.01% (v/v) Antifoam A (Sigma), and 0.01% (w/v) thimerosal] for 60 minutes at room temperature. After blocking, the plates were washed three times with saline-Tween. Fifty μl of PBS, pH 7.2, containing 0.1% Tween-20 and 0.2% (w/v) bovine serum albumin (BSA) was then placed in all wells. Supernatants from wells of the culture plates were replica plated into the corresponding wells of the antigen plates (50 μl/well) and the plates were incubated 30 minutes at room temperature. Supernatants were then removed, the wells washed three times with saline-Tween, and 50 μl of appropriately diluted horseradish peroxidase (HRP) conjugated goat anti-human IgG+IgM (American Qualex International #A1114+#A1124) was added to the wells. In this example, HRP-goat anti-IgG and HRP-goat anti-IgM were used at a final dilution of 1:5000 and 1:3000, respectively, in PBS, pH 7.2, containing 0.05% Tween-20 and 0.1% BSA. Following a 30 minute incubation at room temperature, excess enzyme conjugated goat antibodies were removed and the wells were washed three times with saline-Tween. One hundred μl of substrate (0.8 mg/ml o-phenylenediamine dihydrochloride in 100 mM citrate buffer, pH 5.0, plus 0.03% $H_2O_2$ in deionized $H_2O$, mixed in equal volumes just before plating) was then added to each well. After a 30 minute incubation in the dark, 50 μl of 3N $H_2SO_4$ was added to all wells to terminate reactions. Culture supernatants containing antibodies reacting with the plate's antigen were detected by positive color development in the corresponding wells and the strength of the reaction quantitated by measuring the absorbency at 490 nm on a Bio-Tek EL-310 micro ELISA reader.

Analysis of the culture supernatants by the above method led to the identification of two wells (1C1 and 2H12) which contained anti-*P. aeruginosa* antibodies that reacted with the Fisher immunotypes 3, 5, 6, and 7 plate, but not the Fisher immunotypes 1, 2, and 4 plate or the no-bacteria plate. In order to identify the specific Fisher immunotype(s) recognized, antigen plates containing PLL-fixed bacteria of only one Fisher immunotype were prepared as described above for each immunotype. Performance of the ELISA assay as set forth above with culture supernatants from wells 1C1 and 2H12 on the individual immunotype plates indicated that these two wells contained antibody specific to both Fisher immunotype 3 and 7. A similar ELISA performed on the IATS panel of *P. aeruginosa* typing strains (obtained from A.T.C.C. and included Nos. 33348–33364) demonstrated that antibody in wells 1C1 and 2H12 reacted specifically with IATS strains 2, 5, and 16.

The isotype of the reactive antibody(s) in wells 1C1 and 2H12 was determined in an ELISA assay similar to the specificity tests described above except that the HRP-goat anti-human IgG and HRP-goat anti-human IgM were used independently as second step reagents, rather than being combined. Positive reaction of the antibody(s) in wells 1C1 and 2H12 with Fisher immunotypes 3 and 7 was observed only with the anti-IgM reagents, demonstrating an IgM isotype for the relevant antibody(s) in each well.

In order to determine if the anti-Fisher immunotypes 3 and 7 reaction pattern was due to one or more antibodies in wells 1C1 and 2H12 (i.e., one antibody reactive with both Fisher immunotypes 3 and 7 or two antibodies, one reactive with Fisher immunotype 3 and the other with Fisher immunotype 7) cells from both wells were sub-cultured at low density and wells containing proliferating cells assayed for antibody activity on separate Fisher immunotype 3 and Fisher immunotype 7 bacteria antigen plates. Subculture was performed in 96-well round bottom plates at a density of 5 cells/well in a total volume of 100 μl of HAT medium lacking the aminopterin component (HT-medium). Non-transforming, HAT-sensitive lymphoblastoid cells were included in all wells at a density of 500 cells/well as feeder cells. Four days post-plating, 100 μl of HAT-medium was added to all wells to selectively kill the feeder cells. Wells were again fed on day 9 post-plating by replacement of half the supernatant with HAT medium. Thereafter, wells were similarly fed every 4–5 days with HT-medium until wells were of sufficient lymphoblastoid cell density for supernatant analysis by ELISA. When assayed on individual Fisher immunotype 3 and Fisher immunotype 7 antigen plates, all those supernatants that reacted with Fisher immunotype 3 also reacted with Fisher immunotype 7, indicating that one antibody was responsible for the activity on both Fisher immunotypes. Randomly selected supernatants when assayed on IATS strains 2, 5, and 16 were found to react with all three strains rather than individual strains, further supporting the conclusion that one antibody was cross-reacting with Fisher immunotypes 3 and 7 and IATS strains 2, 5, and 16.

Cloning of specific antibody-producing cells from wells 1C1 and 2H12 was accomplished by independently subjecting the cells from each well to several rounds of limiting dilution cloning until all clonal supernatants assayed by the above ELISA protocol resulted in a positive reaction on Fisher immunotypes 3 and 7 and IATS strains 2, 5, and 16. Cloning employed feeder cells as described above for sub-culturing. By these means, two cloned transformed human cell lines (1C1 and 2H12) were achieved which are continuous (immortal) and which each secrete human monoclonal antibody reactive with Fisher immunotypes 3 and 7 and IATS strains 2, 5, and 16. In this example, the cell line and antibody it produces carry the same designation.

Example II

Example II demonstrates methods for the production of human monoclonal antibody (IgG isotype) that reacts with IATS serotypes 2, 5 and 16 and Fisher immunotypes 3 and 7. The protocols for the production are essentially identical to Example I. Briefly, a peripheral blood sample, obtained from a cystic fibrosis patient known to have had chronic infection with *P. aeruginosa*, served as a source for human B cells. Mononuclear cells were separated as described in Example I, except that 1.6 mls of the PBS suspension were used with $1.6 \times 10^9$ AET-treated sheep red blood cell suspension. Cell driven transformation was also the same, except that: the ratio of 1A2 cells per E⁻PBMC was 7.5; fifteen plates at 17,000 cells/well were used; cultures were fed at 6 and 10 days post-plating; and at sixteen days post-plating, nearly all of the wells contained proliferating cells.

Screening of the culture supernatants for specific antibodies was performed as described, and resulted in locating one well (9D1) that contained an antibody reactive with the Fisher immunotypes 3, 5, 6, and 7 plate, but not the Fisher immunotypes 1, 2 and 4 plate or the no-bacteria plate. Performance of the described ELISA assay on individual immunotype or serotype bacterial antigen plates with 9D1 culture supernatants indicated an antibody specific to both Fisher immunotypes 3 and 7, as well as IATS strains 2, 5 and 6. Subsequent studies performed in accordance with Example I demonstrated that the antibody specificity in well 9D1 was attributable to a single clone secreting IgG isotype antibody.

Example III

Example III demonstrates the antigenic specificity of some of the antibodies of the present invention.

To determine if monoclonal antibodies 1C1, 2H12, and 9D1 reacted with the same antigenic target and were thus identical in specificity, additional assays were performed. First, the antibodies were compared in an ELISA on a panel of reference strains and clinical isolates of *P. aeruginosa*. The ELISA protocol was as described above except for the following modifications: 1) Instead of bacteria adsorbed to PLL coated plates, the wells of the plate contained various whole bacteria that had been ethanol-fixed to the bottom of the well. Plates were prepared by addition of 50 μl of washed bacterial suspension ($OD_{660}=0.2$) in PBS into the wells, centrifugation of the plates for 20 minutes at 500×g, aspiration of PBS, addition of 75 μl of ethanol for 10 minutes, removal of ethanol, followed by air drying. Included on the antigen plates were IATS strains 2, 5, 11, and 16 (A.T.C.C.

Nos. 33349, 33352, 33358, and 33363 respectively) and sixteen clinical isolates that had previously been typed by both agglutination with Difco [Detroit, Mich.] Bacto-Pseudomonas aeruginosa antisera according to the manufacturer's directions and by ELISA (as described herein) as serotypes 2, 5, 16, or a combination of such serotypes; 2) Rabbit typing antisera were used at a dilution of 1:500 in PBS except for anti-IATS 16 which was diluted 1:250. Culture supernatants containing 1C1, 2H12 and 9D1 antibodies were used neat; 3) As second step reagents, biotinylated protein A (B-2001, Vector Laboratories, Inc., Burlingame, Calif.) diluted 1:500 and biotinylated goat anti-human Ig (4703, Tago, Inc., Burlingame, Calif.) diluted 1:500, were used for detection of rabbit and human antibodies respectively. Fifty µl of reagent were added to appropriate wells and after a 30 minute incubation at room temperature, unbound reagent was removed and the wells were washed three times. Fifty µl of a preformed avidin:biotinylated horseradish peroxidase complex (Vectastain ABC Kit, Vector Laboratories, Inc., Burlingame, Calif.) was then added to each well. After a 30 minute incubation at room temperature, the excess Vectastain ABC reagent was removed, and the wells again washed three times before the addition of substrate.

As shown in Table II, results of the assay indicated that whereas antibodies 1C1 and 9D1 reacted with every clinical isolate typed as an IATS 2, 5, or 16 serotype, antibody 2H12 failed to react with three such isolates. This suggests that antibody 2H12 recognized a different epitope from that recognized by 1C1 or 9D1 and that the two epitopes are apparently coordinately expressed on most but not all clinical isolates corresponding to IATS serotypes 2, 5, or 16.

TABLE II

REACTIVITY PATTERNS OF DIFCO BACTO-
P. AERUGINOSA ANTISERA AND HUMAN
MONOCLONAL ANTIBODIES 2H12, 1C1, AND 9D1 ON
TYPE STRAINS AND CLINICAL ISOLATES OF
P. AERUGINOSA

| Type Strain or Clinical Isolate | Rabbit | | | | Human | | |
|---|---|---|---|---|---|---|---|
| | IATS α2 | IATS α5 | IATS α16 | IATS α11 | MAb 2H12 | MAb 1C1 | MAb 9D1 |
| IATS 2 | + | — | — | — | + | + | + |
| IATS 5 | (+)* | + | — | — | + | + | + |
| IATS 16 | (+)* | (+)* | + | — | + | + | + |
| IATS 11 | — | — | — | + | — | — | — |
| A523 | + | + | — | — | + | + | + |
| B406 | + | + | (+)* | — | + | + | + |
| C27 | + | + | — | — | + | + | + |
| D26 | + | + | — | — | + | + | + |
| F155 | + | + | + | — | + | + | + |
| F225 | + | (+)* | + | — | + | + | + |
| F250 | + | + | — | — | + | + | + |
| F253 | — | + | — | — | + | + | + |
| F255 | + | + | — | — | — | + | + |
| F256 | + | — | — | — | — | + | + |
| F396 | + | + | + | — | + | + | + |
| H217 | + | + | — | — | + | + | + |
| H218 | + | + | — | — | + | + | + |
| H219 | — | + | — | — | + | + | + |
| H220 | + | + | — | — | + | + | + |
| H221 | + | + | — | — | — | + | + |

*(+) = ELISA reaction very weakly positive

The data further suggested that the molecular target recognized by antibodies 1C1 and 9D1 was likely to be present on all clinical isolates of P. aeruginosa that could be typed as belonging to IATS serotypes 2, 5, or 16 while the target recognized by antibody 2H12 was expressed on a subgroup of such isolates.

To determine whether the 1C1, 2H12, and 9D1 antibodies reacted with different antigens or alternatively, different epitopes on the same antigen with such epitopes expressed on most but not all IATS 2, 5, and 16 serotypes, immunoblot analysis was performed. Because the shared antigenicity between IATS strains 2, 5, and 16 is apparently due to the heat stable antigens (Liu, P. V. et al., supra) and in keeping with the fact that heat-stability is a previously noted characteristic of lipopolysaccharide molecules, LPS preparations from IATS strains 2, 5, 16, and 11 were chosen as antigen preparations for analysis. Crude LPS was prepared from the type strains by extraction in saline at 60° C. (Orskov, F. et al., Acta. Path. Microbiol. Scand. (1971) Section B 79:142–152). Ten micrograms of LPS, as determined by 2-keto-3-deoxyoctonate (KDO) content (Karkhanis, Y. D., et al., Anal. Biochem. (1978) 85:595–601) from each of the serotypes were subjected to sodium dodecyl sulphate-polyacrylamide gel electrophoresis (SDS-PAGE) (Hancock, R. E. W. and Carey, A. M., J. Bacteriol. (1977) 140:901–910) on a 10–20% gradient gel. Separated molecular species were transferred from the gel to a nitrocellulose membrane (NCM) as described elsewhere (Towbin, H., et al., Proc. Natl. Acad. Sci. USA (1979) 76:4350–4354) and the NCM blot blocked for 1 hr in PBS-Tween (Batteiger, B., et al., J. Immunol. Meth. (1982) 55:297–307). The blots were then incubated for 1 hr at room temperature in 20 ml of spent culture supernatant from either the 1C1, 2H12, or 9D1 cell lines. Following five 5 minute rinses in PBS-Tween, each of the NCM blots was incubated for 1 hr at 25° C. in a 1:1000 or 1:1500 dilution (in PBS-Tween) of alkaline phosphatase-conjugated goat anti-human IgG+IgA+IgM (Zymed). The blots were then subjected to five 5-minute washes in PBS-Tween after which time antigen-antibody interactions were visualized by incubating the blots for 15–20 minutes at 25° C. in 30 ml of nitroblue-tetrazolium/5-bromo-4-chloro-3-indolyl phosphate (NBT-BCIP) substrate as described by Leafy et al., Proc. Natl. Acad. Sct. USA (1983) 80:4045–4049. Color development was stopped by rinsing the blot several times in deionized water.

The blot profiles obtained with the three antibodies were notably different. Antibody 2H12 predominantly recognized a short series of regularly spaced (i.e., ladder-like) low molecular weight molecules in the antigen preparations of serotypes 2, 5, and 16. Some regularly spaced higher molecular weight molecules were also faintly recognized. No reaction was observed on the LPS preparation from serotype 11. A repeat of the immunoblot analysis using LPS preparations that had previously been treated with proteinase K at 60° C. to destroy protein antigens resulted in no alterations in profiles. The low molecular weight bands corresponded precisely with smaller forms of LPS molecules as visualized in a similarly performed SDS-PAGE gel in which the antigens were not transferred to a NCM but were instead specifically stained for the presence of LPS (Tsai, C. M. and Frasch, C. E., Anal. Biochem. (1982) 119:115–119) except that the lowest band on the silver stained gel (representing the core region plus lipid A of LPS) was not recognized. Antibody 1C1 recognized the same series of regularly spaced low molecular weight molecules among antigen preparations of serotypes 2, 5, and 16 but not 11, although the intensity of reaction was not as strong as that with 2H12. In addition, however, this antibody also prominently recognized a series of regularly spaced higher molecular weight molecules on serotypes 2, 5, and 16 which in combination with the recognized lower molecular weight bands, gave rise to distinct, full ladder-like profiles. These profiles were not altered by pretreatment of the antigen preparations with proteinase K. Again, the profiles corresponded to the ladder-like banding patterns observed in LPS-specific stained gels (i.e., they appeared to correspond band for band) except that the band representing core plus lipid A was not recognized. Antibody 9D1 had the same reaction profile as antibody 1C1 on the IATS 2, 5, and 16, but not 11, strains. Again, the bottom-most band of the ladder of a silver stained gel of the different LPS preparations was not recognized and the overall profile was not altered by pretreatment of the LPS preparations with proteinase K. Collectively, these observations indicated that the LPS of serotypes 2, 5, and 16 was the molecular target recognized by the 2H12, 1C1, and 9D1 antibodies.

Example IV

Example IV demonstrates the protective activity of one of the antibodies of the present invention.

To assess the in vivo protective capacity of antibody 1C1, animal protection studies were performed in mice. 1C1 antibody was first concentrated from spent culture supernatant by precipitation with saturated ammonium sulphate (50% final concentration) (Good, A. H., et al., *Selected Methods in Cellular Immunology*, Mishell, B. B. and Shiigi, S. M., eds., W. J. Freeman & Co., San Francisco, Calif., 279–286 (1980)). Precipitated material was reconstituted in a minimum volume of sterile water, extensively dialyzed against PBS, and sterile filtered. As a negative control, spent culture supernatant from another transformed human cell line (6F11-A.T.C.C. No. CRL 8562) producing a human monoclonal antibody specific for the LPS of IATS strain 11 was similarly treated.

Female BALB/c mice between 20 and 22 grams body weight were divided into two groups of thirty mice each. All mice in each group were individually inoculated by the intraperitoneal (ip) route with 0.5 ml of concentrated 1C1 or 6F11 antibody. Six hours later each of the two groups was subdivided into three groups of ten mice and members of each ten mice group were independently challenged ip with 0.3 ml of a live bacterial suspension containing 5 $LD_{50}$ of IATS strain 2, 5, or 11, respectively. Bacterial suspensions were prepared from a broth culture in logarithmic phase growth, from which the bacteria were centrifuged, washed twice in PBS and resuspended to the appropriate density in PBS. Control groups consisting of four or five mice each were injected intraperitoneally with 0.5 ml of PBS and six hours later challenged intraperitoneally with 5 $LD_{50}$ of the same serotypes. After bacterial challenge, animals were then observed for a period of five days.

As shown in Table III, antibody 1C1 provided specific and significant protection against a lethal challenge of both IATS 2 and IATS 5 serotypes, but not the IATS 11 serotype. The typical course following bacterial challenge in all unprotected animals involved varying periods of endotoxic shock and was usually followed by death. Control animals given only PBS went through acute endotoxic shock and all proceeded rapidly to death. Negative control animals given non-homologous antibody (6F11) had a period of more prolonged shock characterized by the symptoms listed in footnote "a" to Table III. Some of these animals eventually recovered, possibly due to the non-antibody components that were co-concentrated in the antibody preparations. The animals which received the protective homologous antibody, however, displayed only minor symptoms of endotoxemia. These symptoms disappeared within 24 hours of innoculation, and the animals then appeared healthy throughout the remainder of the five day observation period.

TABLE III

In Vivo Demonstration of the Protective Effect of Human Monoclonal Antibody 1C1 Against IATS Serotypes 2 and 5

| Human Monoclonal Antibody | No. Survivors/No. of Animals Challenged Five Days After Challenge With: | | |
|---|---|---|---|
| | IATS 2 | IATS 5 | IATS 11 |
| 1C1 | 8/10 | 10/10 | 3/10[a] |
| 6F11 | 0/10 | 1/10[a] | 10/10 |
| PBS | 0/4 | 0/4 | 0/4 |

[a]In those cases where non-specific protection was noted, recovery from infection was markedly different from that seen between homologous antibodies and infecting strains, i.e., 1C1 with IATS 2 or 5 and 6F11 with IATS 11. In the latter cases, recovery was essentially complete with animals appearing normal 24 hours after the bacterial challenge. In non-specific cases, however, mice exhibited signs of acute infection (i.e., diarrhea, crusted eyelids, ruffled fur, "hunched" profile, and slow movement) for several days before recovering to normal status. Such non-specific protection is apparently due to non-antibody components that are co-concentrated and thus injected into the animals, since all animals given only PBS died.

Utilizing the same protocol, a second experiment was performed in which groups of mice were challenged with Fisher strains 2, 3 or 7 and the animals observed for five days. As shown in Table IV, antibody 1C1 again provided specific and significant protection against an otherwise lethal infection with Fisher immunotypes 3 and 7, but was ineffective against Fisher immunotype 2.

TABLE IV

In Vivo Demonstration of the Protective Effect of Human Monoclonal Antibody 1C1 Against Fisher Immunotypes 3 and 7

| Human Monoclonal Antibody | No. Survivors/No. of Animals Challenged Five Days After Challenge With: | | |
|---|---|---|---|
| | Fisher 3 | Fisher 7 | Fisher 2 |
| 1C1 | 10/10 | 10/10 | 1/10[a] |
| 6F11 | 0/10 | 7/10[a] | 10/10 |
| PBS | 0/5 | 0/5 | 0/5 |

[a]Survival most likely due to non-specific protection as described in the footnote to Table III.

Example V

Example V demonstrates a method for the production of a human monoclonal antibody that reacts with IATS serotypes 4 and 11 and Fisher immunotype 2 of *P. aeruginosa*. The process described in Examples I–IV wasa repeated except that it was necessary to make certain modifications to isolate, characterize and assay the antibody described in this Example. The following are the changes in the procedure and the results obtained with the monoclonal antibody described herein.

The source of human B cells was an individual previously immunized with a high molecular weight polysaccharide preparation isolated from Fisher immunotype 3 (Pier, G. B., et al., *Infec. Immun.* [1984] 45:309–313, which is incorporated herein by reference).

Cell-driven transformation of the E⁻PBMC was accomplished by co-cultivating these cells with the transforming cell line 1A2. 1A2 cells in logarithmic growth phase were suspended in HAT medium and then combined with the E⁻PBMC at a ratio of fifteen 1A2 cells per E⁻PBMC. The cell mixture was plated into fourteen microtiter plates at a concentration of 62,000 cells/well in a volume of 200 μl per well. Cultures were fed on days 7 and 11 post-plating, and by day 15 it was observed that 100% of the wells contained proliferating cells.

To screen for the presence of anti-*P. aeruginosa* antibodies, two antigen plates were used which consisted of: (1) a mixture of *P. aeruginosa* Fisher immunotypes 1 through 7 (A.T.C.C. Nos. 27312, 27313, 27314, 27315, 27316, 27317 and 27318, respectively); and (2) a PLL-treated microtiter plate with no bacteria.

Analysis of the culture supernatants by the method of the Examples above led to the identification of approximately 100 wells which contained anti-*P. aeruginosa* antibodies reactive with the Fisher immunotypes 1–7 plate, but not the PLL-treated plate that lacked bacteria. In order to identify the specific Fisher immunotype(s) recognized, antigen plates were constructed as above in which each row of the plates contained PLL-fixed bacteria of only one Fisher immunotype. An ELISA was performed as set forth above, with culture supernatant from each of the anti-*P. aeruginosa* positive wells placed in a columnar array on the new antigen plates resulting in the identification of a number of wells that contained antibody specific for Fisher immunotype 2. To further analyze the serological specificity of the anti-Fisher immunotype 2 antibodies, the supernatants were tested in a similar ELISA on antigen plates constructed to contain each of the seventeen IATS serotypes of *P. aeruginosa* in separate wells. Results of this assay indicated that the great majority of the supernatants were specific for IATS serotype 11 although one supernatant, in well 6D6, demonstrated a cross-reactive specificity pattern on IATS serotypes 4, 11, 13, and 14.

In order to determine if the anti-IATS serotypes 4, 11, 13, and 14 reaction pattern was due to one or multiple antibodies in well 6D6, additional aliquots of supernatant from well 6D6 were independently adsorbed with IATS serotypes 4, 7 (negative control), 11, 13, and 14 and the adsorbed supernatants then tested on PLL-fixed bacteria of each of the five IATS serotypes according to the ELISA assay outlined above. Adsorptions were performed by resuspending a packed bacterial cell pellet with an equal volume of supernatant for one half hour on ice followed by separation of the supernatant from the bacteria by centrifugation. Results of this assay indicated that IATS serotypes 4 and 11 adsorbed out antibody activity against each other, but not against IATS serotypes 7, 13, or 14. This demonstrated the presence of at least two different anti-*P. aeruginosa* antibodies in well 6D6, at least one of which cross-reacted with IATS serotypes 4 and 11.

Isolation and cloning of the appropriate antibody-producing cells from well 6D6 was accomplished in three steps. The first step involved low density subculture of the cells at 20 cells/well and was followed by another round of low density subculture (5 cells/well) of cells obtained from an anti-IATS serotypes 4+11 positive well which had been generated in the first 20 cells/well round of low density subculture. Each round of subculture was performed in 96-well round bottom plates at the stated density in a total volume of 100 μl of HAT medium lacking the aminopterin component (HT-medium). Non-transforming, HAT-sensitive lymphoblastoid cells were included in all wells at a density of 500 cells/well as feeder cells. Four days post-plating, 100 μl of HAT-medium was added to all wells to selectively kill the feeder cells. Wells were again fed on day 9 post-plating by replacement of half the supernatant with HAT medium. Thereafter, wells were similarly fed every 4–5 days with HT-medium until wells were of sufficient lymphoblastoid cell density for supernatant analysis by ELISA as described earlier.

In each assay, those supernatants that were reactive with IATS serotype 4 were also reactive with IATS serotype 11 and Fisher immunotype 2. In addition, antibody activity against IATS serotypes 13 and 14 was lost, thus confirming the earlier specificity assignments.

Formal cloning of specific antibody-producing cells was performed by first plating the cells at very low density (calculated 1/well) into 72-well Terasaki plates (Nunc #1-36538) in a volume of 10 μl/well. Plates were placed in an incubator for 3 hours to allow the cells to settle to the bottom of the plate and then microscopically scored by two different individuals for wells containing a single cell. Each of these cells was then independently placed into the wells of a 96-well round bottom plate with feeder cells and cultured as outlined earlier for low density subculture. Supernatants from all arising clones when assayed by the above ELISA protocol were positive for anti-IATS serotypes 4 and 11.

By these means a cloned transformed human cell line was achieved which grows continuously (is immortal) and secretes human monoclonal antibody reactive with Fisher immunotype 2 and cross-reactive with IATS serotypes 4 and 11. In this example, the cell line and antibody it produces carry the same designation (i.e., 6D6).

The isotype of the antibody in well 6D6 was determined in an ELISA assay similar to the specificity tests described above except that HRP-goat anti-human IgG and HRP-goat anti-human IgM were used independently as second step reagents, rather than being combined. Positive reaction of the antibody in well 6D6 with Fisher immunotype 2 and IATS serotypes 4 and 11 was observed only with the anti-IgM reagent, demonstrating an IgM isotype for this antibody.

Biochemical characterization of the molecular species recognized by the 6D6 antibody was accomplished by immunoblot analysis as described in Example 3 above, except that LPS preparations from Fisher immunotype 2 and IATS serotypes 4 and 11 were chosen as antigen preparations for analysis. An LPS preparation from Fisher immunotype 1 was included as a negative control.

Prior to analysis, each of the crude LPS preparations was diluted 1:1 in dissociation buffer [0.125M Tris, 4% (w/v) sodium dodecyl sulphate (SDS), 20% (v/v) glycerol, 10% (v/v) β-mercaptoethanol, 0.4% (w/v) bromphenol blue, pH 6.8] and bath sonicated for 5 minutes. In order to degrade proteins in the samples, proteinase K (1 mg/ml in $H_2O$) was added to each sample in a 40% (w/w) ratio of enzyme to LPS and incubated at 60° C. for 2 hours with a 5-minute bath sonication step after 1 hour. The samples were then heated to 100° C. for 5 minutes and centrifuged in a microfuge for 2 minutes.

Clarified samples representing 10 μg of LPS from each of the bacterial strains were subjected to SDS polyacrylamide gel electrophoresis (SDS-PAGE) as described above. After transferring the separated molecule species to a NCM, the NCMs were then incubated for 2 hours at room temperature in 10 ml of spent culture supernatant from the 6D6 cell line. The remainder of the procedure was as described above.

Positive results were noted only in the tracks that contained Fisher immunotype 2, IATS serotype 4, or IATS serotype 11LPS. In the Fisher immunotype 2 and IATS serotype 11 tracks, antibody 6D6 recognized a short series of regularly spaced (i.e., ladder-like) low molecular weight molecules which corresponded precisely with smaller forms of LPS molecules as visualized in a similarly performed SDS-PAGE gel in which the antigens were not transferred to a NCM, but were instead specifically stained for the presence of LPS, except that the lowest band on the silver stained gel (representing the core region plus lipid A of LPS) was not recognized. In contrast, in the lane containing IATS serotype 4 LPS, antibody 6D6 recognized a full series of regularly spaced bands nearly spanning the full length of the gel, with the most intense reaction occurring among the higher molecular weight bands. Again, this profile corresponded to the ladder-like banding pattern observed in the LPS-specific stained gel (i.e., they appeared to correspond band for band), with the exception that the band representing core plus lipid A was not recognized. These data clearly indicated that the O-side chain of LPS was the molecular target recognized by antibody 6D6 on Fisher immunotype 2 and IATS serotypes 4 and 11.

To assess the in vivo protective capacity of antibody 6D6, animal protection studies were performed in mice. The 6D6 antibody was first concentrated from spent culture supernatant by precipitation with saturated ammonium sulphate (50% final concentration). Precipitated material was reconstituted in a minimum volume of sterile water, extensively dialyzed against PBS, and sterile filtered. As a negative control, spent culture supernatant from another transformed human cell line (C5B7-A.T.C.C. No. CRL 8753) producing a human monoclonal antibody specific for the LPS of Fisher immunotype 1 was treated in the same manner. Similarly, as a positive control, spent culture supernatant from transformed human cell line 6F11 (A.T.C.C. No. CRL 8562) producing a human monoclonal antibody specific for the LPS of Fisher immunotype 2 and IATS serotype 11 was concentrated.

Female Swiss-Webster mice between 20 and 22 grams body weight were divided into three groups of twenty mice each. All mice in each group were individually inoculated by the intraperitoneal (ip) route with 0.5 ml of concentrated 6D6, C5B7, or 6F11 antibody. Six hours later, each of the three groups was subdivided into four groups of five mice and members of each five-mice group were independently challenged ip with 0.3 ml of a live bacterial suspension containing 8 $LD_{50}$ of Fisher immunotype 1, Fisher immunotype 2, IATS serotype 4 or IATS serotype 11, respectively. Bacterial suspensions were prepared as described above in Example IV. After bacterial challenge, the animals were observed for a period of five days. Results were as follows:

TABLE V

In Vivo Demonstration of the Protective Effect of
Human Monoclonal Antibody 6D6 Against
Fisher Immunotype 2 and IATS Serotypes 4 and 11

| Human Monoclonal Antibody | No. Survivors/No. Tested Five Days After Challenge With: | | | |
|---|---|---|---|---|
| | Fisher 1 | Fisher 2 | IATS 4 | IATS 11 |
| 6D6 | 0/5 | 5/5 | 4/5 | 5/5 |
| 6F11 | 0/5 | 5/5 | 0/5 | 5/5 |
| C5B7 | 5/5 | 1/5 | 0/5 | 0/5 |

As shown in Table V, antibody 6D6 provided specific and significant protection against a lethal challenge of Fisher immunotype 2, IATS serotype 4, and IATS serotype 11, but not Fisher immunotype 1.

Example VI

Example VI demonstrates a method for the production of a human monoclonal antibody that reacts with IATS serotypes 6 and 13 and Fisher immunotype 1 of P. aeruginosa. The process described in Examples I through V was repeated, except that it was necessary to make certain modifications to isolate, characterize and assay the antibody described in this Example. The following are the changes in the procedures and the results obtained with the monoclonal antibody described herein.

The source of human B cells was an individual previously immunized with a high molecular weight polysaccharide preparation isolated from Fisher immunotype 2 (Pier et al., Infec. Immun., 34:461 (1981)). After collecting the E⁻PBMC, as described above, the cells were frozen in FCS containing 10% (v/v) DMSO in a liquid nitrogen vapor tank. These cells were later thawed quickly at 37° C., washed once in Iscove's medium and resuspended in HAT medium. Cell-driven transformation was accomplished at a ratio of 15 1A2 to cells per E⁻PBMC. The Cell mixture plated into 20 microtiter plates at a concentration of 78,500 cells/well. Cultures were fed every 3–5 days post-plating and at eleven days it was observed that 100% of the wells contained proliferating cells.

To screen supernatants for the presence of anti-P. aeruginosa antibodies using the ELISA technique, the antigen plate consisted of a mixture of P. aeruginosa Fisher immunotypes 1–7 [clinical isolate PSA 1277 (Genetic Systems Corporation Organism Bank ("GSCOB")), ATCC 27313, PSA G98 (GSCOB), ATCC 27315, PSA F625 (GSCOB), ATCC 27317 and ATCC 27318, respectively]. A PLL-treated microtiter plate with no bacteria was also used in the screen.

Analysis of the culture supernatants by the above method lead to the identification of approximately 200 wells which contained anti-P. aeruginosa antibodies reactive with the Fisher immunotypes 1–7 plate, but not the PLL-treated plate that lacked bacteria. In order to identify those wells that contained antibody reactive with two or more IATS serotypes, antigen plates were constructed, as above, in which a column of the plates contained PLL-fixed bacteria of only one IATS serotype. An ELISA was performed, as set forth above, with supernatant from an expanded culture of each of the anti-P. aeruginosa positive wells. Supernatants were placed in a row on the new antigen plates and resulted in the identification of a number of wells that contained antibody reactive with multiple IATS serotypes. One well, designated 8H7, contained antibodies specific for IATS serotypes 6 and 13. When the supernatant from this well was tested by ELISA on the 7 Fisher immunotypes, as in Example V, it was demonstrated that the antibodies of 8H7 were specific for Fisher immunotype 1.

In order to determine if the anti-IATS serotypes 6 and 13 reaction pattern was due to one of multiple antibodies in well 8H7, additional aliquots of supernatant were independently adsorbed with IATS serotypes 6, 13, and 17 (negative control), and the adsorbed supernatants then tested on PLL-fixed bacteria of each of the three IATS serotypes according to the ELISA assay outlined above. Results indicated that IATS serotypes 6 and 13 adsorbed out antibody activity against each other. IATS serotype 17 adsorbed out no activity against either IATS 6 or 13. This data demonstrated that the anti-IATS serotype 6 and 13 reaction pattern was due to a single antibody from well 8H7.

Isolation and cloning of the antibody-producing cells from well 8H7 was accomplished in three steps, essentially as described in Example V above. By these means a cloned transformed human cell line was achieved which grows continuously (i.e., is immortal) and secretes human monoclonal antibody reactive with Fisher immunotype 1 and cross-reactive with IATS serotypes 6 and 13. In this example, the cell line and antibody it produces carry the same designation, 8H7. Using a procedure similar to that described in Example V, the isotype of the antibody in well 8H7 was determined to be IgM.

Biochemical characterization of the molecular species recognized by the 8H7 antibody was accomplished by immunoblot analysis as described in Examples III and V above, except that the LPS preparations from Fisher immunotype 1 and IATS serotypes 6 and 13 were chosen as antigen preparations for analysis. An LPS preparation from IATS serotype 10 was included as a negative control.

Analysis of the resulting immunoblots showed positive results only in the NCM tracks that contained Fisher immunotype 1, IATS serotype 6, or IATS serotype 13 LPS. In the Fisher immunotype 1 and IATS serotype 6 tracks, antibody 8H7 recognized a series of regularly spaced (i.e., ladderlike) bands spanning nearly the full length of the gel. These bands corresponded precisely with the multiple molecular weight forms of LPS molecules, as visualized in a similarly performed SDS-PAGE gel in which the antigens were not transferred to a NCM, but were instead specifically stained for the presence of LPS. In the lane containing IATS serotype 13 LPS, antibody 8H7 recognized a more abbreviated series of regularly spaced bands confined to the mid-to-upper molecular weight range of the gel. Again, the bands which were recognized corresponded in position to those observed in an LPS-specific stained gel, except that the highest and lowest molecular weight forms of LPS in the stained gel did not appear to be well-recognized in the Western blot. These data clearly indicated that LPS was the molecular target recognized by antibody 8H7 on Fisher immunotype 1 and IATS serotypes 6 and 13.

To assess the in vivo protective capacity of antibody 8H7, animal protection studies were performed in mice, as described in Examples IV and V above. As a negative control, spent culture supernatant from another transformed human cell line (6F11—ATCC No. CRL 8652), producing a human monoclonal antibody specific for the LPS of Fisher immunotype 2, was treated in the same manner. As a positive control, spent culture supernatant from transformed human cell line C5B7 (ATCC No. CRL 8753), producing a human monoclonal antibody specific for the LPS of Fisher immunotype 1 and IATS serotype 6, was used.

Female Swiss-Webster mice between 20 and 22 grams body weight were divided into three groups of 30 mice each. All mice in each group were individually inoculated intraperitoneally (ip) with 0.5 ml of concentrated 8H7, 6F11, or C5B7 antibody. Four hours later, each of the three groups was subdivided into three groups of ten mice and members of each ten-mice group were independently challenged ip with 0.3 ml of a live bacterial suspension containing $9.4LD_{50}$ of a clinical isolate (A522) representative of the IATS 6 serotype (Fisher immunotype 1 equivalent), $5LD_{50}$ of the IATS 13 reference serotype, or $10LD_{50}$ of the IATS 11 (Fisher immunotype 2 equivalent) reference serotype. Bacterial suspensions were prepared as described above in Example IV. After bacterial challenge, the animals were observed for a period of five days. Results were as follows:

TABLE VI

In Vivo Demonstration of the Protective Effect of Human Monoclonal Antibody 8H7 Against IATS Serotypes 6 and 13

| Human Monoclonal Antibody | Number Survivors/Number Tested, Five Days After Challenge With: | | |
|---|---|---|---|
| | IATS 6 | IATS 13 | IATS 11 |
| 8H7 | 9/10 | 6/10 | 1/10 |
| C5B7 | 9/10 | 0/10 | 0/10 |
| 6F11 | 0/10 | 2/10 | 10/10 |

As shown in Table VI, antibody 8H7 provided specific and significant protection against a lethal challenge of IATS serotype 6, but not IATS serotype 11. The protection against IATS serotype 13 was to a lesser degree, but may be explained by the relatively high number of organisms required to achieve the $LD_{50}$ for this isolate when compared to the serotype 6 isolate ($3 \times 10^7$ colony forming units and $2.6 \times 10^6$ colony forming units, respectively). In a separate experiment, antibody 8H7 protected five of five mice challenged with $3.5LD_{50}$ of the IATS 13 isolate and five of five mice challenged with the IATS 6 isolate.

From the foregoing, it will be appreciated that the cell lines of the present invention provide human monoclonal antibodies and fragments thereof cross-reactive for and cross-protective against various P. aeruginosa IATS serotypes. This allows prophylactic and therapeutic compositions to be more easily developed that can be effective against infections due to most, if not all, P. aeruginosa strains. In addition, the cell lines provide antibodies which find uses in immunoassays and other well-known procedures.

Although the present invention has been described in some detail by way of illustration and example for purposes of clarity of understanding, it will be obvious that certain changes and modifications may be practiced within the scope of the appended claims.

We claim:

1. A method for inhibiting the viability of Pseudomonas aeruginosa organisms, comprising:

exposing said P. aeruginosa, in the presence of complement and neutrophils, to a viability inhibiting amount of a human monoclonal antibody or binding fragment thereof which specifically binds to an accessible determinant of outer membrane of P. aeruginosa lipopolysaccharide IATS serotype 2 and 5 and Fisher immunotype 3, wherein said monoclonal antibody inhibits the viability of organisms of at least two of said IATS serotypes and immunotype in the presence of the complement and neutrophils.

2. The method of claim 1, wherein the monoclonal antibody further binds to and inhibits the viability of P. aeruginosa organisms of Fisher immunotype 7.

3. The method of claim 1, wherein the monoclonal antibody has the antigen binding specificity of a monoclonal antibody obtained from ATCC CRL 8941.

4. The method of claim 3, wherein the monoclonal antibody is obtained from ATCC CRL 8941.

5. The method of claim 1, wherein the monoclonal antibody inhibits the viability of organisms in the presence of human complement and human neutrophils.

6. The method of claim 1, wherein the monoclonal antibody further binds specifically to P. aeruginosa organisms of IATS serotype 16.

7. A method for inhibiting the viability of Pseudomonas aeruginosa organisms, comprising:

exposing said P. aeruginosa, in the presence of complement and neutrophils, to a viability inhibiting amount of a human monoclonal antibody or binding fragment thereof obtained from ATCC CRL 9171 which specifically binds to an accessible determinant of outer membrane lipopolysaccharide of P. aeruginosa IATS serotype 4 and 11 and Fisher immunotype 2.

8. The method of claim 7, wherein the complement and neutrophils are human.

9. A method for inhibiting the viability of Pseudomonas aeruginosa organisms, comprising:

exposing said P. aeruginosa, in the presence of complement and neutrophils, to a viability inhibiting amount of a human monoclonal antibody or binding fragment thereof obtained from ATCC CRL 9258 which specifically binds to an accessible determinant of outer membrane lipopolysaccharide of P. aeruginosa IATS serotype 6 and 13 and Fisher immunotype 1.

10. The method of claim 9, wherein the complement and neutrophils are human.

* * * * *